Figure 1:
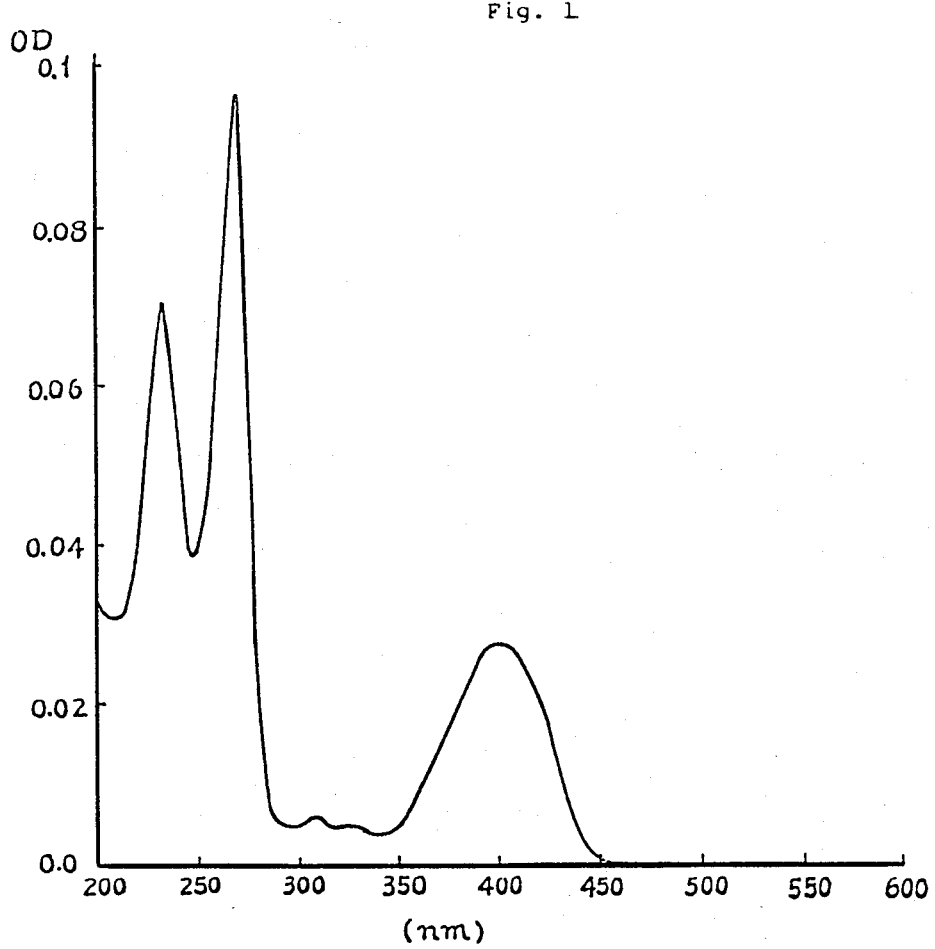

United States Patent [19]

Tomita et al.

[11] Patent Number: 4,511,560
[45] Date of Patent: Apr. 16, 1985

[54] ANTIBIOTIC SUBSTANCES DC-45, AND THEIR USE AS MEDICAMENTS

[75] Inventors: Fusao Tomita; Tatsuya Tamaoki; Kunikatsu Shirahata, all of Machida; Takao Iida, Tokyo; Makoto Morimoto, Numazu; Kazuhisa Fujimoto, Shizuoka, all of Japan

[73] Assignee: Kyowa Hakko Kogyo Kabushiki Kaisha, Tokyo, Japan

[21] Appl. No.: 412,693

[22] Filed: Aug. 30, 1982

Related U.S. Application Data

[63] Continuation-in-part of Ser. No. 259,386, May 1, 1981, abandoned, which is a continuation-in-part of Ser. No. 200,299, Oct. 24, 1980, abandoned.

[30] Foreign Application Priority Data

Oct. 26, 1979 [JP] Japan ................................ 54-137734

[51] Int. Cl.³ ...................... A61K 31/71; C07H 15/26; C12P 19/56
[52] U.S. Cl. ..................................... 514/27; 435/169; 536/16.8; 536/18.1
[58] Field of Search ............................. 536/16.8, 18.1; 424/181

[56] References Cited

U.S. PATENT DOCUMENTS 4,393,056 7/1983 Tomita et al. ....................... 536/16.8

OTHER PUBLICATIONS

Brockman et al., "Chem. Abst." vol. 70, 1969, p. 97116(y).

Primary Examiner—Johnnie R. Brown
Attorney, Agent, or Firm—Wolder, Gross & Yavner

[57] ABSTRACT

New substances designated as DC-45-A, DC-45-B₁ and DC-45-B₂ and represented by the following general formula:

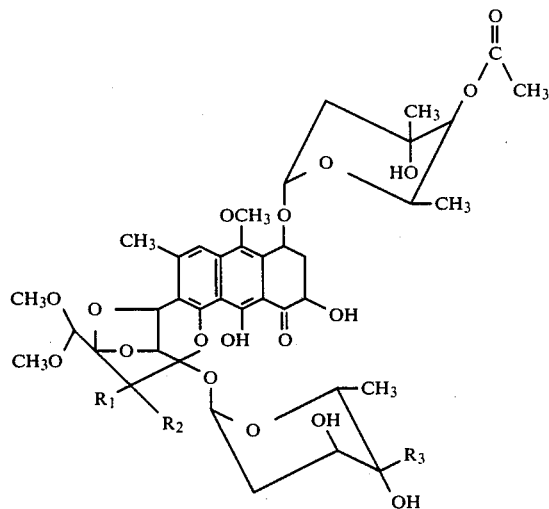

wherein (i) $R_1$ and $R_2$ together with the carbon atom therebetween represent the group

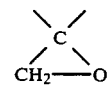

and $R_3$ represents

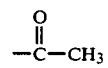

(designated DC-45-A); (ii) $R_1$ represents —OH, $R_2$ represents —CH$_2$OH and $R_3$ represents

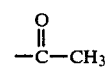

(designated DC-45-B₁); or (iii) $R_1$ and $R_2$ together with the carbon atom therebetween represent the group (Abstract continued on next page.)

and R₃ represents
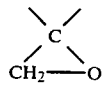
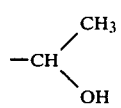
(designated DC-45-B₂).
DC-45-A, DC-45-B₁ and DC-45-B₂ possess antibiotic and anti-tumor activity and may be obtained by culturing a microorganism of the genus Streptomyces. Preferred strain is *Streptomyces bottropensis* (FERM-P No. 5219; NRRL 12051).
5 Claims, 6 Drawing Figures

ANTIBIOTIC SUBSTANCES DC-45, AND THEIR USE AS MEDICAMENTS

RELATED APPLICATIONS

This application is a continuation-in-part of Ser. No. 259,386, filed May 1, 1981, now abandoned, which is a continuation-in-part of Ser. No. 06/200,299, filed Oct. 24, 1980, now abandoned by the present inventors.

DESCRIPTION

This invention relates to substances having antibiotic activity, processes for their preparation, pharmaceutical composition containing the same and their use as medicaments. The substances of this invention are designated DC-45, and more particularly they are represented by the following general formula (I):

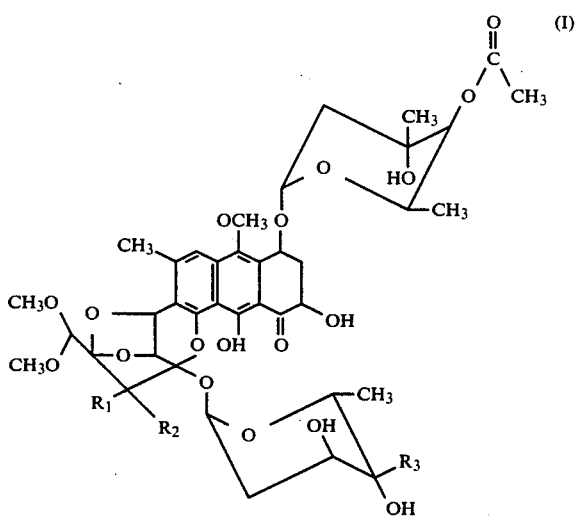

wherein (i) $R_1$ and $R_2$ together with the carbon atom therebetween represent the group

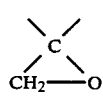

and $R_3$ represents

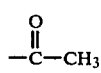

(designated DC-45-A); (ii) $R_1$ represents —OH, $R_2$ represents —CH$_2$OH and $R_3$ represents

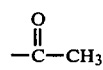

(designated DC-45-B$_1$); or (iii) $R_1$ and $R_2$ together with the carbon atom therebetween represent the group

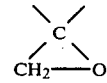

and $R_3$ represents

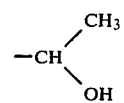

(designated DC-45-B$_2$).

Figure 2:
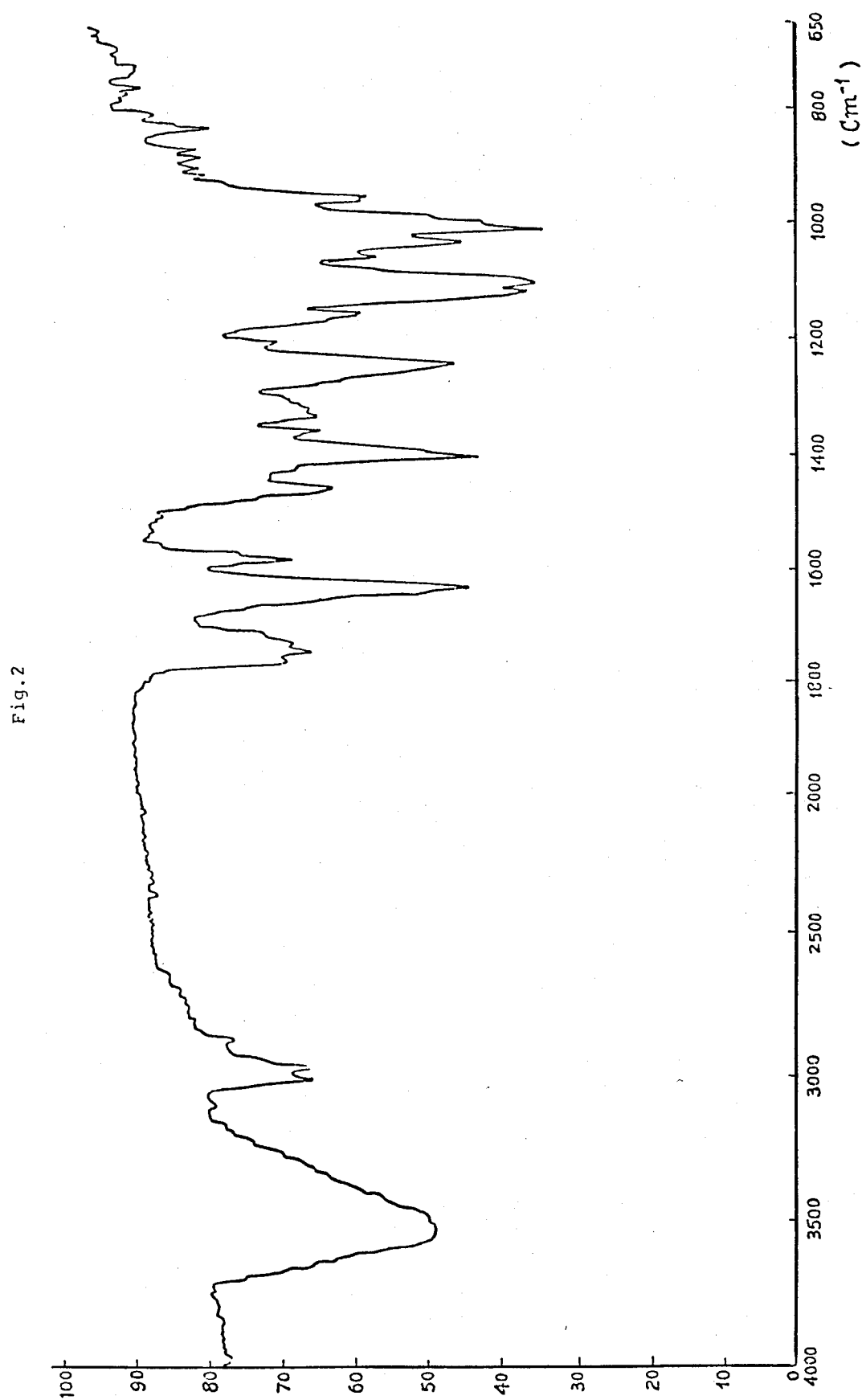
Figure 3:
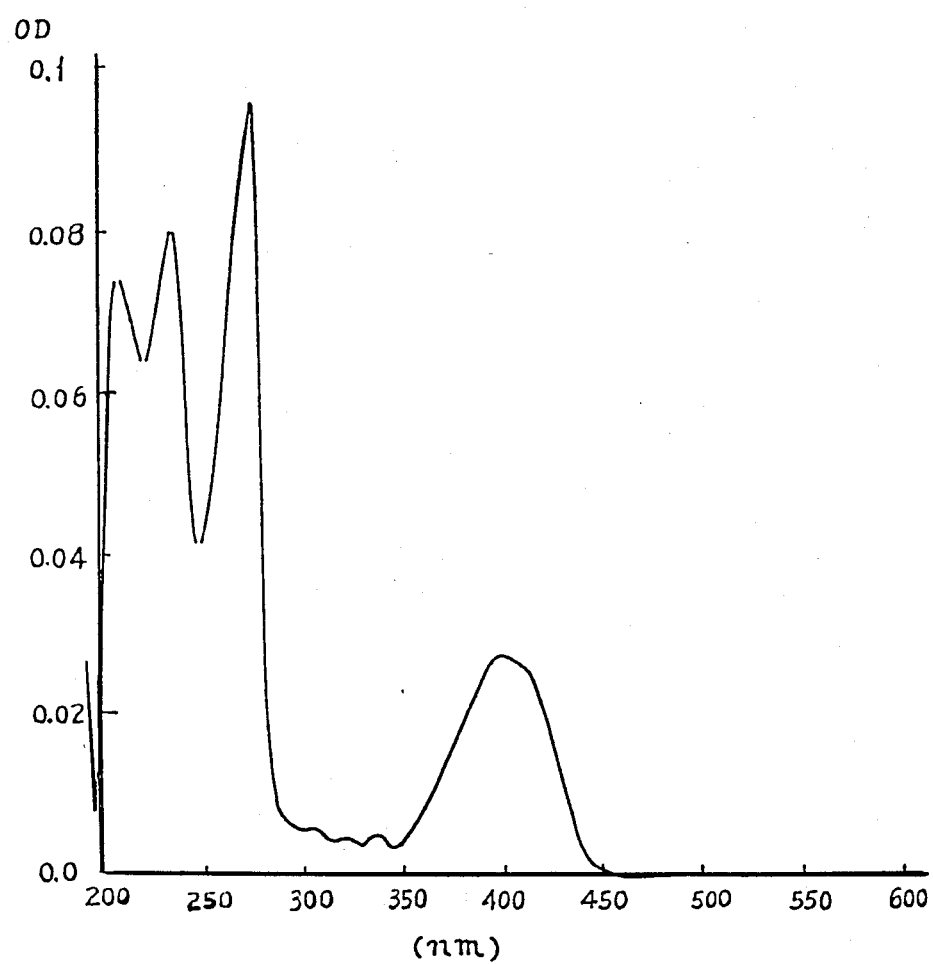
Figure 4:
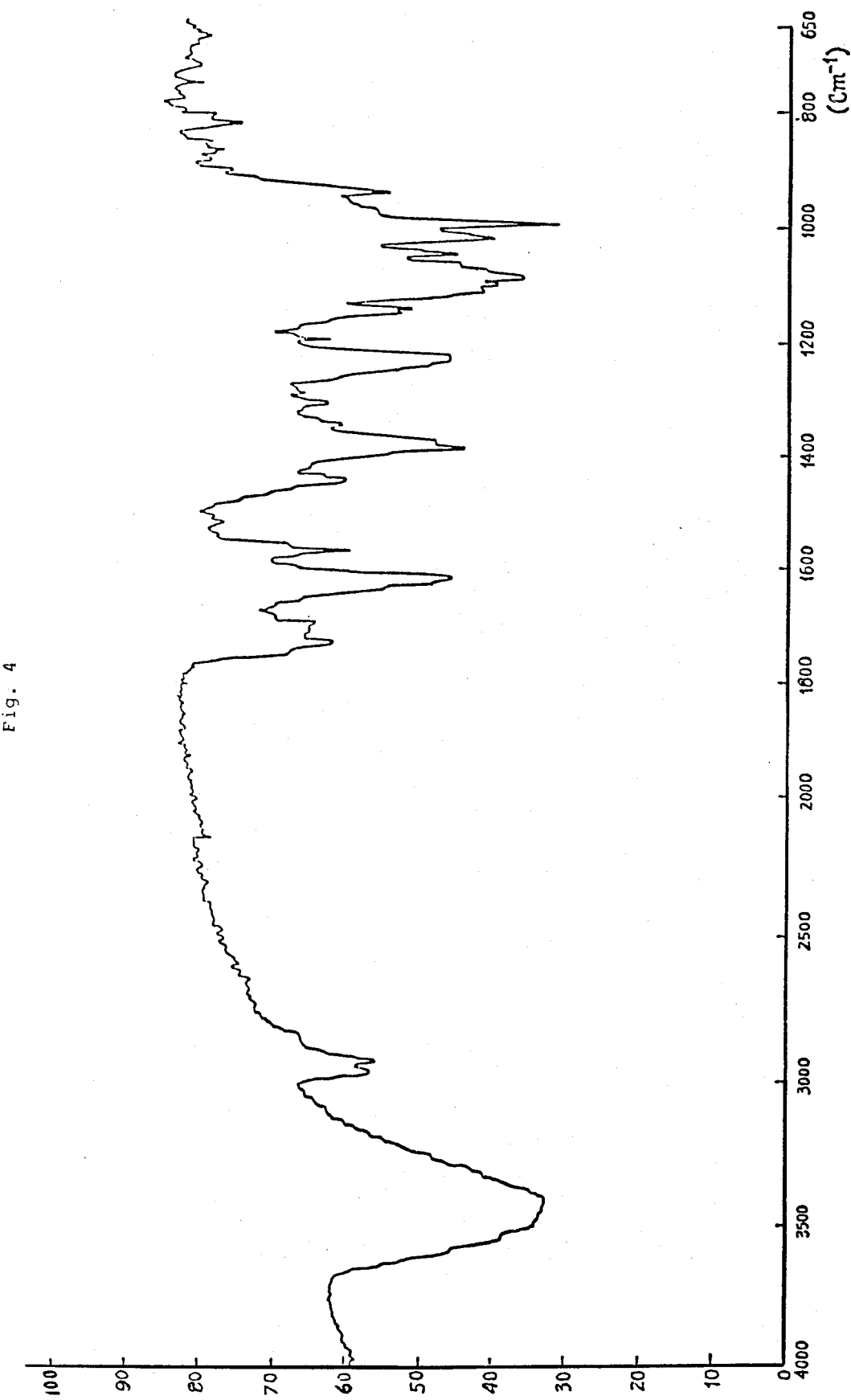

The physico-chemical characteristics of DC-45-A and DC-4-5-B$_2$ according to this invention are as follows:

(1) DC-45-A (1) Elemental analysis: H:5.74%, C:55.11%
(2) Molecular weight: 877
(3) Molecular formula: $C_{42}H_{52}O_{20}$
(4) Melting point: 180° C.±3° C. (decomposed)
(5) Ultraviolet absorption spectrum: As shown in FIG. 1 (in 50% methanol)
(6) Infrared absorption spectrum: As shown in FIG. 2 (KBr tablet method)
(7) Specific rotation: $[\alpha]_D^{25} = -15.3°$ (c=1.0, ethanol)
(8) PMR spectrum (in CDC$_3$; ppm): 1.07 (3H,s); 1.10 (3H, d, J=6.8); 1.24 (3H,d, J=6.5); many peaks between 1.40–2.30; 2.14 (3H,s); 2.49 (3H,s); 2.63 (3H,s); many peaks between 2.30–2.80; 2.91 (1H,d, J=5.6); 3.00 (1H,d, J=5.6); 3.49 (3H,s); 3.63 (3H,s); 3.85 (3H, s); many peaks between 3.60–4.00; 4.18 (1H,s); 4.55 (1H,q, J=6.8); many peaks between 4.70–4.90; 5.03 (1H, q, J=6.5); 5.25 (1H,d, J=4.0); 5.39 (1H, d, J=4.0); 5.87 (1H, m); 7.52 (1H,s); 14.1 (1H,s)
(9) CMR spectrum (in CDCl$_3$; ppm): 210.9; 203.8; 170.3; 162.1; 152.5; 145.2; 142.3; 135.3; 126.7; 117.0; 114.2; 108.3; 105.3; 99.7; 97.2; 93.7; 85.1; 79.0; 74.6; 71.1; 69.6; 69.3; 68.8; 67.9; 66.3; 64.0; 62.8; 57.3; 55.9; 36.5; 32.2; 28.0; 25.7; 20.9; 20.2; 17.0; 14.7
(10) Solubility: Soluble in methanol, ethanol, water and chloroform; slightly soluble in acetone and ethyl acetate, and insoluble in ether and n-hexane

Figure 5:
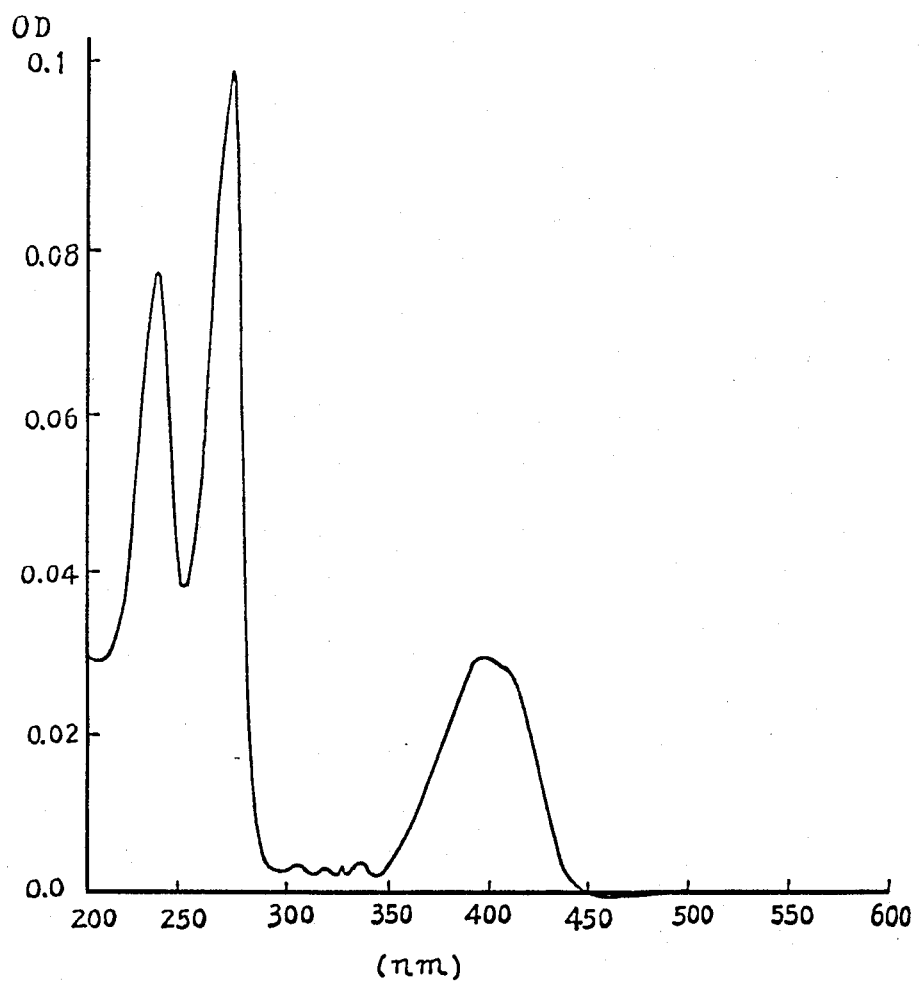
Figure 6:
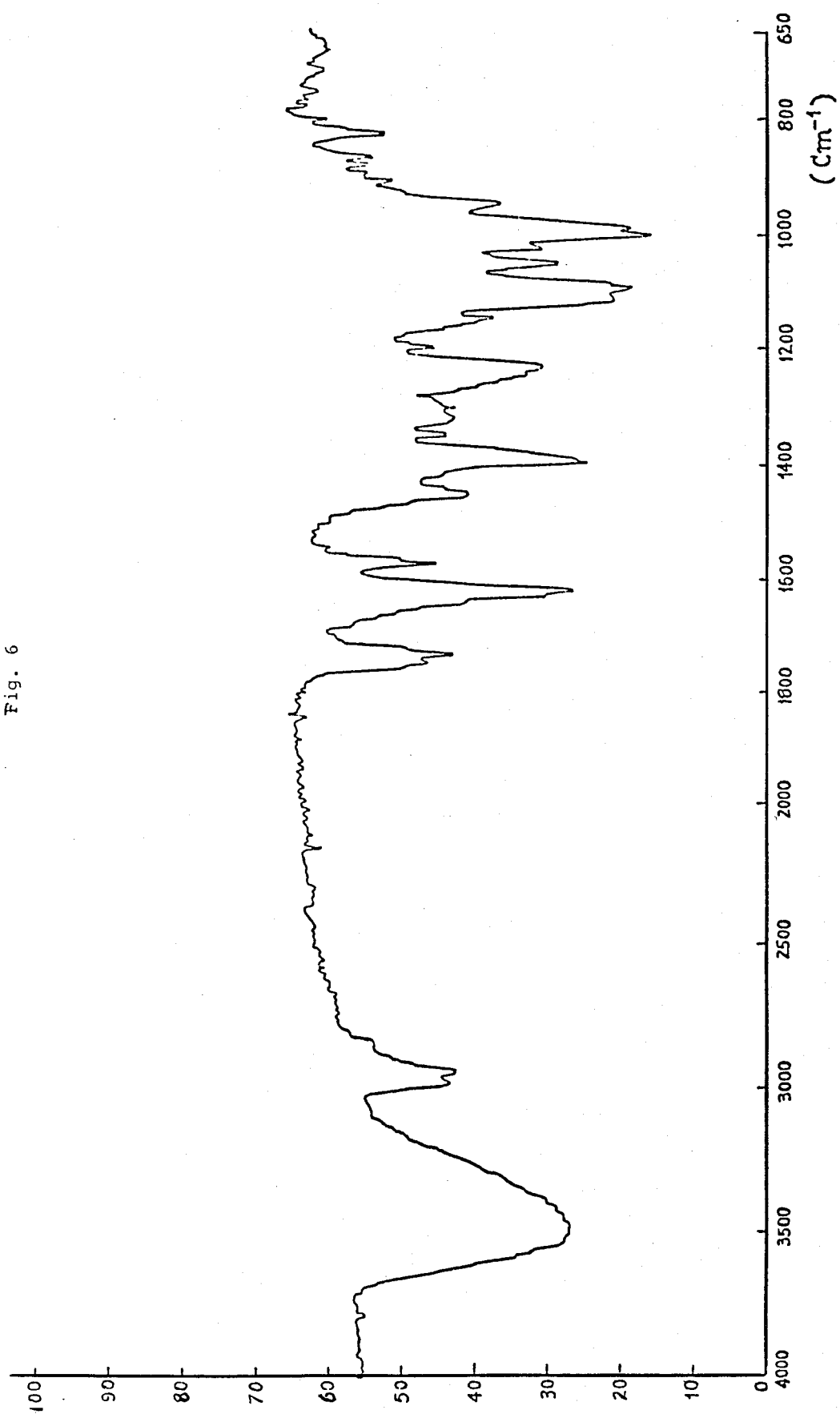

(2) DC-45-B$_2$ (1) Elemental analysis: H: 6.03%, C: 54.34%
(2) Molecular weight: 879
(3) Molecular formula: $C_{42}H_{54}O_{20}$
(4) Melting point: 181°–182° C. (decomposed)
(5) Ultraviolet absorption spectrum: As shown in FIG. 5 (in 95% ethanol)
(6) Infrared absorption spectrum: As shown in FIG. 6 (KBr tablet method)
(7) Specific rotation: $[\alpha]_D^{25} = -10°$ (c=0.2, ethanol)
(8) PMR spectrum (in CDCl$_3$; ppm): 1.07 (3H,s); many peaks between 1.07–1.5; many peaks between 1.50–2.80; 2.14 (3H,s); 2.61 (3H, broad s); 2.86 (1H, d, J=5.7); 2.96 (1H, d, J=5.7); 3.46 (3H,s); 3.63 (3H, s); 3.84 (3H, s); many peaks between 3.65–4.20; many peaks between 4.40–5.00; many peaks between 5.10–5.50; 5.80 (1H, broad s); 7.49 (1H, d, J=1.0); 14.1 (1H, s)
(9) CMR spectrum (in CDCl$_3$; ppm): 202.8; 170.2; 163.1; 151.8; 144.8; 142.9; 135.4; 126.5; 116.8; 114.9; 107.3; 104.6; 101.5; 99.6; 98.0; 94.4; 74.4; 72.5; 71.4; 70.4;

69.1; 68.8; 68.3; 67.9; 67.5; 66.4; 62.9; 62.7; 56.8; 56.5; 48.0; 36.7; 32.3; 25.7; 20.8; 20.3; 18.2; 16.9; 15.5

(10) Solubility: Soluble in methanol, ethanol, acetone, ethyl acetate and chloroform; slightly soluble in benzene, ether and water; and insoluble in n-hexane.

The figures attached are as follows:

| FIG. No. | Ultraviolet absorption spectrum | Infrared absorption spectrum |
|---|---|---|
| 1 | DC-45-A | |
| 2 | | DC-45-A |
| 3 | DC-45-B$_1$ | |
| 4 | | DC-45-B$_1$ |
| 5 | DC-45-B$_2$ | |
| 6 | | DC-45-B$_2$ |

The Rf values of the substances DC-45-A, DC-45-B$_1$ and DC-45-B$_2$ as hereinbefore defined are shown in Table 1 and were determined by thin layer chromatography using silica gel (Kieselgel 60 Art. 5721, commercial product of E. Merck, West-Germany) and developed for 3 hours at room temperature.

TABLE 1

| No. | Solvent system | Substance | Rf |
|---|---|---|---|
| 1. | Chloroform/methanol = 90:10 (v/v) | DC-45-A | 0.85 |
| | | DC-45-B$_1$ | 0.50 |
| | | DC-45-B$_2$ | 0.45 |
| 11. | Ethyl acetate/acetic acid = 90:10 (v/v) | DC-45-A | 0.70 |
| | | DC-45-B$_1$ | 0.25 |
| | | DC-45-B$_2$ | 0.35 |
| 111. | Upper layer of mixture of 0.1 M phosphate buffer (PH: 7.0) and ethyl acetate | DC-45-A | 0.70 |
| | | DC-45-B$_1$ | 0.30 |
| | | DC-45-B$_2$ | 0.40 |

DC-45 can form a salt with a metal such as an alkali metal, an alkaline earth metal and aluminum. Therefore, pharmacologically acceptable salts of DC-45 such as the sodium salt, potassium salt, calcium salt, magnesium salt, aluminum salt etc. also fall into the scope of the invention. Such a salt can be prepared by reacting DC-45-A, DC-45-B, or DC-45-B$_2$, with a hydroxide or an alkoxide of a suitable metal.

According to a still further feature of this invention, there is provided a pharmaceutical composition for human or veterinary use comprising as active ingredient a substance according to the present invention as hereinbefore defined in association with a pharmacologically acceptable carrier or excipient. The composition may be presented in a form suitable for oral, rectal or parenteral administration. Thus, for example, composition for oral administration may be solid or liquid and may be in the form of granules, tablets, coated tablets, capsules, syrups, emulsions, suspensions or drops, such composition comprising carriers or excipients conventionally used in the pharmaceutical art. Thus, for example suitable tabletting excipients include lactose, potato and soluble starches and magnesium stearate.

For parenteral administration, the carrier may be a sterile, parenterally acceptable liquid such as e.g. water, or a pharmaceutically acceptable oil e.g. arachis oil, contained in ampoules.

Composition for rectal administration may take the form of suppositories, the carrier comprising a suppository base. Advantageously, the composition may be formulated as dosage units, each being adapted to supply a fixed dose of the active ingredient. Tablets, coated tablets, capsules, suppositories and ampoules are examples of suitable dosage unit forms.

The active ingredient may be a salt of DC-45-A, DC-45-B$_1$ and/or DC-45-B$_2$, for example, with an alkali metal, alkaline earth metal, aluminum and the like such as sodium, potassium, calcium, magnesium, aluminum and the like, which may be prepared by using a hydroxide or alkoxide of a suitable metal in conventional manner.

The present invention also provides a substance as hereinbefore defined for use as an antibiotic or antitumour agent.

The anti-biotic activity of the substance DC-45-A, DC-45-B$_1$ and DC-45-B$_2$ are shown in Table 2, the activity being determined by the agar dilution method at pH7.0.

TABLE 2

| | Minimum Inhibitory Concentration (μg/ml) | | |
|---|---|---|---|
| DC-45 | A | B$_1$ | B$_2$ |
| Staphylococcus aureus ATCC 6538P | 0.2 | 50 | 0.4 |
| Bacillus subtilis No. 10707 | 0.01 | 12 | 0.01 |
| Klebsiella pneumoniae ATCC 10031 | 1.5 | >100 | 1.5 |
| Salmonella typhosa ATCC 9992 | 50 | >100 | >100 |
| Escherichia coli ATCC 26 | 12 | >100 | 50 |

Acute toxicities of DC-45-A, DC-45-B$_1$ and DC-45-B$_2$

The LD$_{50}$ values of DC-45-A, DC-45-B$_1$ and DC-45-B$_2$ are respectively 1, 100 and 2 mg/kg (mouse-i.p.).

Anti-tumour activities of DC-45-A, DC-45-B$_1$ and DC-45-B$_2$ (1) Therapeutic effect on Sarcoma 180 solid tumour:

Mice (male; ddy-strain; weight about 20 g; each group consisting of 6 mice) were used as test animals. Sarcoma 180 tumour cells (each $5 \times 10^6$ cells) were subcutaneously implanted into each mouse at the armpit. 24 hours after this, a phosphate buffered physiological solution of sodium chloride (each 0.2 ml) was intraperitoneally administered to each mouse, a given amount of one of the substances DC-45-A, DC-45-B$_1$ and DC-45-B$_2$ being contained in each solution so that a different substance is administered to each group of mice. The said phosphate buffer contained NaCl (0.8 g/dl), KCl (0.02 g/dl), NaHPO$_4$ (1.15 g/dl) and KH$_2$PO$_4$ (0.02 g/dl). For comparison purpose, a similar phosphate buffered solution containing mitomycin C (0.2 ml) was abdominally administered to the mice of another group 24 hours after the implantation of the tumour cells. Table 3 indicates the volume of the tumour (mean value in mm$^3$) and T/C (mean value; the tumour volume of the animal treated with the test compound/the tumour volume of the control animal treated with 0.2 ml of the phosphate buffered solution of sodium chloride, both being determined 7 days after the implantation.

TABLE 3

| Test substance | Dose (mg/kg) | Volume of tumour (mean value) mm$^3$ | T/C |
|---|---|---|---|
| DC-45-A | 0.2 | 775 | 0.55 |
| | 0.1 | 930 | 0.66 |
| | 0.2* | 592 | 0.42 |
| | 0.1* | 846 | 0.60 |
| DC-45-B$_1$ | 75 | 775 | 0.55 |
| | 50 | 846 | 0.60 |
| | 20 | 1057 | 0.75 |
| DC-45-B$_2$ | 1.0 | 493 | 0.35 |

TABLE 3-continued

| Test substance | Dose (mg/kg) | Volume of tumour (mean value) mm$^3$ | T/C |
|---|---|---|---|
| | 0.5 | 1170 | 0.83 |
| Mitomycin C | 5.6 | 282 | 0.20 |
| Untreated | 0 | 1410 | — |

Note:
*Continued for 7 days (once daily)

(2) Anti-tumour activity of substances DC-45-A, DC-45-B$_1$ and DC-45-B$_2$ on Lymphocytic leukaemia p-388 tumour:

Mice (male; CDF$_1$ strain; weight about 22 g; each group consisting of 5 mice) were used as the test animals. Lymphocytic leukaemia P-388 tumour cells (each $1 \times 10^6$ cells) were intraperitoneally implanted into each mouse. 24 hours after this, a phosphate buffered physiological solution of sodium chloride (each 0.2 ml) was intraperitoneally injected once into each mouse, a given amount of one substance being contained in each solution so that a different substance is administered to each group of mice. For comparison, a similar phosphate buffered solution of sodium chloride containing mitomycin C was admnistered abdominally to each mouse of a further control group. Table 4 indicates the average survival time in days and T/C (mean value of the survival days of the animals treated with the test compound/mean value of the survival days of the control animals treated with 0.2 ml of the phosphate buffered solution of sodium chloride).

TABLE 4

| Substance | Dose (mg/kg) | Survival days | T/C |
|---|---|---|---|
| Untreated | — | 9.6 ± 0.9 | — |
| DC-45-A | 0.2* | 11.3 ± 0.8 | 1.18 |
| | 0.1* | 13.0 ± 0.9 | 1.35 |
| DC-45-B$_1$ | 50 | 15.5 ± 1.7 | 1.62 |
| | 20 | 14.2 ± 1.5 | 1.48 |
| | 12.5 | 15.0 ± 1.4 | 1.56 |
| DC-45-B$_2$ | 1.0 | 12.0 ± 2.0 | 1.25 |
| | 0.5 | 12.8 ± 2.2 | 1.33 |
| | 0.25 | 12.2 ± 0.8 | 1.27 |
| Mitomycin C | 5.6 | 18.0 ± 1.4 | 1.88 |

Note:
Continued once daily for 5 days

The substances of this invention have been prepared by investigating the substances produced by culturing various microorganisms which we have collected from natural sources. Thus, the antibiotic substances of this invention, designated as DC-45-A, DC-45-B$_1$ and DC-45-B$_2$ have been isolated from the culture broth obtained by culturing a microorganism, which we have isolated from the soil in Sapporo City, Japan.

Thus according to a further feature of this invention, there is provided a process for the preparation of a substance having activity against *Bacillus subtilis* No. 10707, which comprises culturing a microorganism of the genus Streptomyces capable of producing a substance as defined in any one of claims 1 to 2 in a culture medium to accumlate the said substance in the cultured broth and recovering the said substance therefrom.

Any and all microorganisms of the genus Streptomyces capable of producing the substances designated DC-45 may be used for the process of this invention, preferably microorganisms of the species *Streptomyces bottropensis* DO-45 (FERM-P No. 5219; NRRL 12051) as hereinafter described.

Taxonomical characteristics of *S. bottropensis* DO-45 (FERM-P No. 5219; NRRL 12051)

(A) Morphological characteristics:

Aerial myceria are well formed and appear to be simply branched and spiral, when the above-listed strain is cultured in a conventional medium. Spores are in the form of chains having more than 10 links. The spore surface is smooth. Spores are ellipsoidal (0.4–0.5 $\mu \times 0.7$–0.8 $\mu$). Table 5 indicates the degree of growth, colour on the surface, colour at the back of colonies and colour of soluble pigment, which are observed by culturing the above-titled strain using various media. The colour classification described in Color Harmony Manual published by Container Corpn. of America is used for colour identification.

TABLE 5

| Media | Growth | Colour of colonies Surface | Colour of colonies Back | Growth & colour of aerial mycelium | Soluble pigment |
|---|---|---|---|---|---|
| Sucrose-nitrate agar | good, flat | oatmeal (2 ec) | oatmeal (2 ec) | moderate natural string (2 de) | nil |
| Glucose-asparagine agar | good, flat | light rose beige (4 ec) | mustard (2 le) | poor natural (3 dc) | cinnamon (3 lc) |
| Glycerin-asparagine agar | good, raised | shell (3 ca) | shell (3 ca) | nil | nil |
| Starch-inorganic salt agar | moderate, flat | pussy willow gray (5 dc) | sand (3 cb) | moderate white (a) | camel (3 ie) |
| Tyrosin agar | good, flat | yellow tint (1 ba) | ivory tint (2 cb) | nil | nil |
| Nutrient agar | poor, flat | camel (3 ie) | bamboo (2 gc) | nil | camel (3 ie) |
| Yeast-malt extract agar | good, raised | rose beige (4 ge) | mustard (2 le) | poor white (a) | chestnut brown (4 nil) |
| Oatmeal agar | good, raised | oatmeal (2 ec) | oatmeal (2 ec) | good covert gray (2 fe) | nil |
| Peptone-yeast-iron agar | good, flat | oatmeal (2 ec) | oatmeal (2 ec) | nil | clove brown |

TABLE 5-continued

| | | Growth on various media | | | |
|---|---|---|---|---|---|
| | | Colour of colonies | | Growth & colour of | Soluble |
| Media | Growth | Surface | Back | aerial mycelium | pigment |
| | | | | | (3 ni) |

(B) Physiological characteristics:

The physiological characteristics of *Streptomyces bottropensis* FERM-P No. 5219 (NRRL 12051) are set out in the following where the results were determined after culturing for 2 weeks at 27° C. with the exception that the optimum temperature was determined after 5 days and the actions upon milk and cellulose were determined after one month.

| (1) | Utilization of carbon sources: | |
|---|---|---|
| | Carbon sources | Assimiliability |
| | D-arabinose | + |
| | D-xylose | ++ |
| | D-glucose | ++ |
| | D-fructose | ++ |
| | Sucrose | ++ |
| | Inositol | ++ |
| | L-rhamnose | + |
| | Raffinose | ++ |
| | D-mannit | ++ |
| (2) | Liquefaction of gelatin | − |
| (3) | Action upon milk: | |
| | Liquefaction | ± |
| | Coagulation | − |
| | Peptonization | − |
| (4) | Decomposition of cellulose | slightly positive |
| (5) | Hydrolysis of starch | positive |
| (6) | Optimum growth pH | 6.8–7.5 |
| (7) | Optimum growth temperature | 28–38° C. |
| (8) | Production of tyrosinase | − |
| (9) | Production of melanoid pigment | − |

From these characteristics, the above-mentioned microorganism may be classified into the genus Streptomyces. This strain resembles closely in morphological and physiological characteristics to the species *Streptomyces parvulus* in reliance with the classification by E. Küster [Intern. J. System. Bacteriol., vol. 22, No. 3, page 139 (1972)] because its aerial mycellium is grayish. However, the microorganisms of the geus *S. parvulus* are not capable of metabolizing raffinose and thus, this microorganism is apparently different from *S. parvulus*. As a result, the present strain was designated *S. ochraceus* DO-45 in view of the color of its vesitative mycelia. The present strain has been deposited with Bikoken (the Fermentation Institute) of 1-1-3, Higashi Yatabe-cho, Tsukuba-gun, Ibaraki-ken, Japan as FERM-P No. 5219 and also with the Northen Regional Research Center, Agricultural Research North Central Region, Peoria, Ill., U.S.A. as NRRL 12051. However, as a result of further studies, it has been found that even though the present strain is somewhat similar to *S. parvulus*, *S. collinus* and *S. bottropensis*, it is different from *S. parvulus* and *S. collinus* because *S. parvulus* does not produce melanoid pigment and *S. collinus* possesses strong spore chains and few spirals. On the other hand, the present strain is generally quite similar to *S. bottropensis* except a minor difference that *S. bottropensis* produces melanoid pigment on peptone-yeast extract-iron-agar medium and tyrosine-agar medium and also is almost incapable of metabolizing raffinose. However, such a minor difference is not enough to distinguish the present strain from *S. bottropensis*. Thus, the present strain is found to be identical with *S. bottropensis* and the designation of the present strain has been changed to *S. bottropensis*. Any and all microorganisms of the species *S. bottropensis* and their mutant strains capable of producing the substance of the present invention may be used for the purpose of the present invention, although a preferred strain is of the species *S. bottropensis* as hereinafter described.

Method of fermentation of S. bottropensis (FERM-P No. 5219; NRRL 12051)

Any and all conventional methods for culturing the strains of the genus Streptomyces may be used for the purpose of the present invention. Various nutrients as exemplified below may be used for fermentation. For example, as the carbon sources, glucose, starch, dextrin, mannose, fructose, sucrose, lactose, xylose, arabinose, mannitol, molasses and the like may be used solely, or in combination, although it is possible to use, depending upon the assimilability of the strain used, various hydrocarbons, alcohols and organic acids.

As the nitrogen sources, various inorganic and organic nitrogen-containing compounds such as, for example, ammonium chloride, ammonium sulfate, ammonium nitrate, sodium nitrate and urea may be used, although it is possible to use various natural nitrogen sources such as peptone, meat extract, yeast extract, dry yeast, corn steep liquor, soybean meal and casamino acid, which may be used solely or in combination. If desired, various inorganic salts such as sodium chloride, potassium chloride, magnesium sulfate, calcium carbonate, potassium monohydrogen phosphate, potassium dihydrogen phosphate, ferrous sulfate, calcium chloride, magnesium sulfate, zinc sulfate, copper sulfate and the like may be used. Moreover, vitamin $B_1$, biotin and other trace components may conveniently be used to promote the growth of the microorganism and to enhance the production of the compounds of this invention. Liquid culturing procedure, in particular, submerged culturing with stirring are preferred for fermentation of the microorganism here concerned. The fermentation is preferably effected at a temperature of 25°–40 ° C. (for example 28°–38° C.) at a pH of 4–10 (for example 6–8) which may be adjusted by using aqueous ammonia or ammonium carbonate solution. In general, the compounds of this invention may be produced and accumlated in the culture broth by effecting the liquid culture for one to seven days. The fermentation is, of course, preferably continued until the amount of each or all of the desired compounds of this invention in the cultured broth reach their maximum. Then the fermentation is discontinued and the cultured liquor is filtered to separate the microbial cells from the liquor.

The compounds of this invention may be isolated from the filtrate and purified by methods conventionally used for isolation and purification of metabolic products present in the cultured liquor of mocroorganisms. For example, a cell-free filtrate having a pH of 6.0 is passed through a column packed with a non-ionic porous resin (e.g. Diaion HP-20, a commercial product of Mitsubishi Kasei Kogyo K.K., Tokyo) to absorb the active substance onto the resin, from which the active substance is eluted by using, for example, methanol, acetone or ethyl acetate. The eluted fractions are concentrated to dryness. Cellite powders are used to absorb the active substance, and the powders are applied onto a column packed with silica gel which has been suspended in n-hexane and ethyl acetate (1:1 v/v). A mixture of n-hexane and ethyl acetate (1:1 v/v) is passed through the column to remove impurities and the column is eluted with a mixture of n-hexane and ethyl acetate (1:5 v/v) to elute the fractions containing the compound designated DC-45-A. By subsequent elution with ethyl acetate, fractions containing a mixture of the compounds designated DC-45-$B_1$ and DC-45-$B_2$ may be obtained. Fractions containing DC-45-A are concentrated to dryness in vacuo. The residue is chromatographed by using a column packed with silica gel which is in advance suspended in chloroform. At first, impurities are removed by passing chloroform through the column and then a mixture of chloroform and methanol (100:1 v/v) is passed through the column so that DC-45-A is eluted. The eluate is concentrated to dryness. The residue is taken up with chloroform and the insoluble substances are removed by centrifugation of filtration. n-Hexane is added to the solution to precipitate DC-45-A. The precipitate is separated and dried to obtain powders of DC-45-A. Other fractions containing DC-45-$B_1$ and DC-45-$B_2$ are concentrated and chromatographed by using a column packed with silica gel which is in advance suspended in chloroform. Chloroform and a mixture of chloroform/methanol (100:1 v/v) are successively passed through the column to remove impurities, and the elution is effected by using a mixture of chloroform/methanol (50:1 v/v) to obtain a mixture of DC-45-$B_1$ and DC-45-$B_2$. The eluate is concentated to dryness and transferred to a column packed with slica gel which is in advance suspended in a mixed solution of a 0.1M phsphate buffer (pH 7.0) and ethyl acetate. The elution is effected by using a similar layer to that described above so that DC-45-$B_1$ and DC-45-$B_2$ are eluted in this order, sufficiently separated from each other. Respective fractions are individually collected and concentrated. The residues are respectively taken up with ethyl acetate and insoluble substances are removed. Acetone is added to the solution of DC-45-$B_1$ and the precipitate is separated and dried to obtain powders of DC-45-$B_1$. n-Hexane is added to the solution of DC-45-$B_2$ and the precipitate is separated and dried to obtain powders of DC-45-$B_2$.

It is also possible to isolate the desired compounds DC-45-A, DC-45-$B_1$ and DC-45-$B_2$ from the microbial cells by extacting the cells with acetone, concentrating the extract to dryness, and treating the residue in a similar manner to that described above, namely by silica gel chromatography.

The following non-limiting examples illustrate the invention, in which the compounds DC-45-A, DC-45-$B_1$ and DC-45-$B_2$ were identified by bioassay using *Bacillus subtilis* No. 10707 or in reliance with yellowish colour of the compounds.

EXAMPLE 1

*Streptomyces botrropensis*

(FERM-P-5219) (NRRL 12051) was used as the seed strain and was inoculated into a seed medium [300 ml; containing KCl (4 g/l), $MgSO_4 7H_2O$ (0.5 g/l), $KH_2PO_4$ (1.5 g/l), ammonium sulfate (5 g/l), sucrose (20 g/l), fructose (10 g/l) glucose (10 g/l), corn steep liquor (5 g/l), $CaCO_3$ (20 g/l); pH 7.0]in a 2 liter Erlenmeyer flask. The fermentation was effected at 30° C. for 48 hours with stirring (220 r.p.m.) to obtain a seed culture which was transferred into a 30 liter jar fermentor containing a medium (15 liter; having the composition as hereinafter defined) at a ratio of 5% (v/v). The fermentation was effected at 30° C. for 72 hours with shaking and aeration (250 r.p.m.; 15 liter/min). The pH of the medium was not controlled during the fermentation. Composition of the fermentation medium:

Glucose (30 g/l), soluble starch (10 g/l),
Farmamedia (cotton seed meal, commercial product of Traders Oil Mill Co., U.S.A.; (10 g/l),
$K_2HPO_4$ (1 g/l), $M_gSO_4.7H_2O$ (1 g/l), NaCl (3 g/l), $CuSO_4.5H_2O$ (70 mg/l), $FeSO_4.7H_2O$ (10 mg/l), $MnCl_2.4H_2O$ (8 mg/l), $ZnSO_4.7H_2O$ (2 mg/l), $CoCl_2O$ (0.006 mg/l); pH 7.0 before sterilization, adjusted with NaOH.

After completion of the fermentation, the microbial cells and precipitates were removed from the cultured broth by filtration, resulting in a filtrate (13 l). The filtrate was passed through a column packed with one liter of a non-ionic porous resin (Diaion HP-10, commercial product of Mitsubishi Kasei Kogyo KK., Tokyo) to absorb the active substances onto the resin which was then washed with water (about 2 liter), followed by washing with 50% (v/v) methanol (about 2:1) to remove impurities. After this, the elution was effected using methanol. The methanol fraction (about one liter) was concentrated to dryness in vacuo, and the residue was dissolved in 0.1M phosphate buffer (pH 7.0) and extracted three times with ethyl acetate. The ethyl acetate layer was concentrated and adsorbed onto Cellite to obtain a powder.

Separately the microbial cells (about 200 g, wet basis) were suspended in acetone (about 5 l) to extract the desired substances. The extract was concentrated to dryness in vacuo and the residue was dissolved in a 0.1M phosphate buffer solution (pH 7.0). The solution was extracted three times with ethyl acetate. The ethyl acetate layer was concentrated and then mixed with Cellite to give a powder. The powder was gently put on a column packed with silica gel (Wako Gel, commercial product of Wako Junyaku K.K., Japan; 500 ml) which had been suspended in n-hexane/ethyl acetate (1:1 v/v) was passed through the column to remove impurities. The elution was effected using a solvent system of n-hexane/ethyl acetate (1:5 v/v) to obtain fractions containing DC-45-A. By subsequent elution using ethyl acetate, there was obtained fractions containing both DC-45-$B_1$ and DC-45-$B_2$. They were respectively collected and concontrated to dryness. The residue containing DC-45-A was chromatographed by using a column packed with silica gel which had been suspended in chloroform in the following manner:Chloroform was passed through the column to remove impurities, and then a mixture of chloroform/methanol (100:1 v/v) was used for elution. DC-45-A was eluted and separated from impurities, and the solution thus obtained was concentrated. The residue was dissolved in chloroform and the insoluble substances were removed by filtration. N-hexane was added to the filtrate. The resultant precipitate was separated and dried to obtain DC-45-A in the form of powder (10 mg).

Fractions containing a mixture of DC-45-$B_1$ and DC-45-$B_2$ were chromatographed by passing chloroform through a column packed with silica gel which had been suspended in chloroform, followed by passing a solvent system of chloroform/methanol (100:1 v/v) through the same column so as to remove impurities. Then a chloroform/methanol mixture (50:1 v/v) was used for elution of a mixture of DC-45-B$_1$ and DC-45-B$_2$. The eluate was concentrated to dryness and the residue was gently put onto a column packed with silica gel which had been suspended in the organic layer of a solvent mixture of 0.1M phosphate buffer (pH 7.0) and ethyl acetate. A similar layer was used for elution and DC-45-B$_2$ and DC-45-B$_1$ were eluted in this order. These fractions were respectively collected and concentrated to dryness. The residues were respectively dissolved in ethyl acetate to remove insoluble substances. Acetate was added to the solution containing DC-45-B$_1$, and the precipitate was separated and dried to obtain DC-45-B$_1$ (10 mg) in the form of powder. N-hexane was added to the solution containing DC-45-B$_2$ to give a precipitate which was separated and dried to obtain DC-45-B$_2$ in the form of powder (5 mg).

The physico-chemical characteristics of the compounds of this invention thus-obtained and their anti-tumour and anti-biotic activities are as hereinbefore described.

EXAMPLE 2

Analogous treatments to those described in Example 1 were carried out except the use of a fermentation medium having the following composition so that DC-45-A (5 mg), DC-45-B$_1$ (5 mg) and DC-45-B$_2$ (3 mg) were obtained.

Composition of the medium:

Soluble starch (40 g/l), defatted soybean meal (30 g/l), corn steep liquor (5 g/l), K$_2$HPO$_4$ (0.5 g/l), MgSO$_4$.7H$_2$O (0.5 g/l), KCl (0.3 g/l), CaCO$_3$ (3 g/l); pH 7.8 before sterilization, adjusted with NaOH.

We claim:

1. A substance having antibiotic activity and selected from the group consisting of DC-45-A, DC-45B$_1$ and DC-45-B$_2$ represented by the following formula:

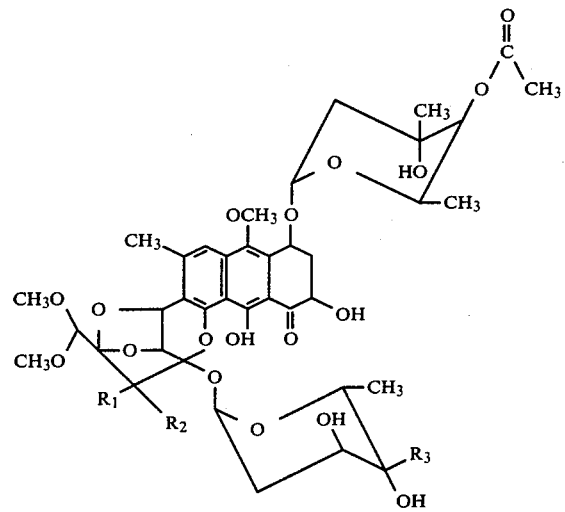

wherein (i) R$_1$ and R$_2$ together with the carbon atom therebetween represent the group

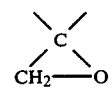

and R$_3$ represents

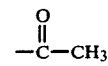

(designated DC-45-A); (ii) R$_1$ represents —OH, R$_2$ represents —CH$_2$OH and R$_3$ represents

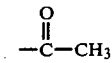

(designated DC-45-B$_1$); or (iii) R$_1$ and R$_2$ together with the carbon atom therebetween represent the group

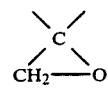

and R$_3$ represents

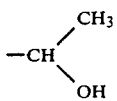

(designated DC-45-B$_2$) or a pharmaceutically acceptable salt thereof.

2. The substance of claim 1 wherein the said salt is in the form of a metal salt selected from the group consisting of alkali metal salt, alkaline earth metal salt and aluminum salt.

3. A pharmaceutical composition for use as an antibiotic comprising as active ingredients an effective amount of at least one substances as claimed in claim 1, in association with a pharmacologically acceptable carrier or excipient.

4. The pharmaceutical composition of claim 3 suitable for parenteral administration wherein said carrier is a parenterally acceptable liquid.

5. The pharmaceutical composition of claim 3, wherein said active ingredient is in the form of a metal salt selected from the group consisting of alkali metal, alkaline earth metal and aluminum.

* * * * *